United States Patent [19]

Ota

[11] Patent Number: 4,694,121
[45] Date of Patent: Sep. 15, 1987

[54] PRINTED CIRCUIT BOARD

[75] Inventor: Masuaki Ota, Chiba, Japan

[73] Assignee: Sony Corporation, Tokyo, Japan

[21] Appl. No.: 929,396

[22] Filed: Nov. 10, 1986

[30] Foreign Application Priority Data

Nov. 8, 1985 [JP] Japan .................................. 60-248710

[51] Int. Cl.⁴ .............................................. H05K 3/34
[52] U.S. Cl. ................................... 174/68.5; 228/103; 228/180.2; 361/409
[58] Field of Search ...................... 228/103, 179, 180.1, 228/180.2; 174/68.5; 361/403, 409

[56] References Cited

U.S. PATENT DOCUMENTS 3,887,760  6/1975  Kreiger et al. .............. 228/180.2 X
4,139,881  2/1979  Shimizu et al. .............. 228/180.1 X
4,339,784  7/1982  Shearer ........................... 174/68.5 X
4,467,638  8/1984  Greenstein ...................... 228/103 X
4,529,116  7/1985  Gutbier ......................... 228/180.1 X

FOREIGN PATENT DOCUMENTS 2729834  1/1979  Fed. Rep. of Germany ..... 174/68.5
52-29691  3/1977  Japan .................................. 228/103

Primary Examiner—R. R. Kucia
Attorney, Agent, or Firm—Hill, Van Santen, Steadman & Simpson

[57] ABSTRACT

A printed circuit board having an electrically insulative substrate, an electroconductive layer formed on the electrically insulative substrate, and a resist layer formed on the electroconductive layer which has a row of openings whose distances between adjacent ones increase from one end to the other end of the row.

6 Claims, 10 Drawing Figures 4,694,121

PRINTED CIRCUIT BOARD

BACKGROUND OF THE INVENTION

1. Field of the Invention

This invention relates generally to printed circuit boards, and particularly to such a printed circuit board with which solderability can be checked easily by observing a checking pattern provided thereon.

2. Description of the Prior Art

There are various ways of preventing solder bridgings from occuring between land portions on a printed circuit board, when a printed circuit board having electronic parts mounted thereon is dipped in a solder bath for soldering lead terminals of the electronic parts with the land portions on the printed circuit board.

FIG. 1 is a top plan view of a printed circuit board of a prior art whose land portions are arranged to prevent solder bridging from occuring (Examined Japanese Patent Publication No. 58-2470), and FIG. 2 is an enlarged cross-sectional view along a line V—V in FIG. 1 showing that an electronic part is soldered on the printed circuit board.

In FIGS. 1 and 2, reference numeral 21 designates a printed circuit board which includes an insulative substrate 22, an electroconductive layer 23, and a resist layer 26. The electroconductive layer 23 is coated on the insulative substrate 22. The resist layer 26 is coated on the electroconductive layer 23 in such a manner that a short land portion 24A and a long land portion 24B are formed adjacent to each other. Further, a through-hole or opening 25 is provided at a central portion of each of the land portions 24A and 24B. The through-holes 25 penetrate the electroconductive layer 23 and the insulative substrate 22 so that a lead terminal pin 28 of an electronic device e.q. an integrated circuit (IC) 27 is inserted into the through-holes 25. Provided that the length from the through-hole 25 of the short land portion 24A to its one end is $l_1$ and the length from the through-hole 25 of the long land portion 24B to its one end is $l_2$, the relation between $l_1$ and $l_2$ are selected to satisfy, $2l_1 \leq l_2 \leq 3l_1$. Accordingly, the line drawn by connecting one end of the land portions 24A and 24B makes a saw tooth line in the direction of an arrow A.

When the printed circuit board of FIG. 1 is moved in the direction of an arrow B and dipped in a solder bath (not shown) to solder the lead terminal pins 28 of the IC 27 to the through-holes 25 at the land portions 24A and 24B, each of the land portions 24A and 24B departs from the surface of melted solder at different timings, so that solder bridging does not occure between the land portions 24A and 24B which are adjacent to each other in the direction of the arrow A.

Although the solder bridging does not occure between the land portions 24A and 24B on the printed circuit board 21 by carrying out the soldering in the above described manner, it is very difficult to examine wettability of the solder for performing a good soldering without solder bridging. Therefore, in this printed circuit board the wettability was adjusted on the basis of an operator's experience, knowledge and so on by observing a conditon of a solder 29. Thus, the soldering condition, that is, the wettability of the solder differs depending upon the judgement of an operator. It may therefore be supposed that the lead terminal pins 28 of the IC 27 are soldered on the land portions 24A and 24B differently, as shown in FIGS. 3A, 3B, and 3C, dependent upon the different wettability of solder.

FIG. 3A shows a case where the wettability of solder is small. In this case, cavity 29A is formed around the terminal pin 29 and on the layer 23 inside the solder 29. Connection between the solder 29 and the terminal pin 28, and the layer 23 seems to be in a good condition for a while after soldering, however, the solder 29 may come off by secular variation.

FIG. 3B shows a case where the wettability of solder is adequate or optimum, and the soldering is satisfactorily made.

FIG. 3C shows a case where the wettability of solder is large. Thus, connection of the solder 29 to the lead terminal 28 and the layer 23 is made with a small amount of solder, so that the soldering strength is not enough.

It has therefore been desired to provide a printed circuit board by which the wettability of solder can be checked in a simple manner since the wettability is a parameter to determine whether or not the soldering can be satisfactorily made.

OBJECTS AND SUMMARY OF THE INVENTION

An object of the present invention is to provide a printed circuit board by which solderability or wettability of solder can be checked easily.

To achieve the above object, the present invention provides a printed circuit board which comprises:

an electrically insulative substrate;

an electroconductive layer formed on the electrically insulative substrate; and a resist layer formed on the electroconductive layer and having a row of openings, distances between adjacent openings increasing from one end to another end of the row.

The above and other objects, features and advantages of the present invention will become apparent from the following detailed description of the preferred embodiment taken in conjunction with the accompanying drawings, throughout which like reference numerals designate like elements and parts.

DESCRIPTION OF THE PREFERRED EMBODIMENT

Now, an embodiment of a printed circuit board according to the present invention will hereinafter be described with reference to FIGS. 4 and 5.

Figure 1:
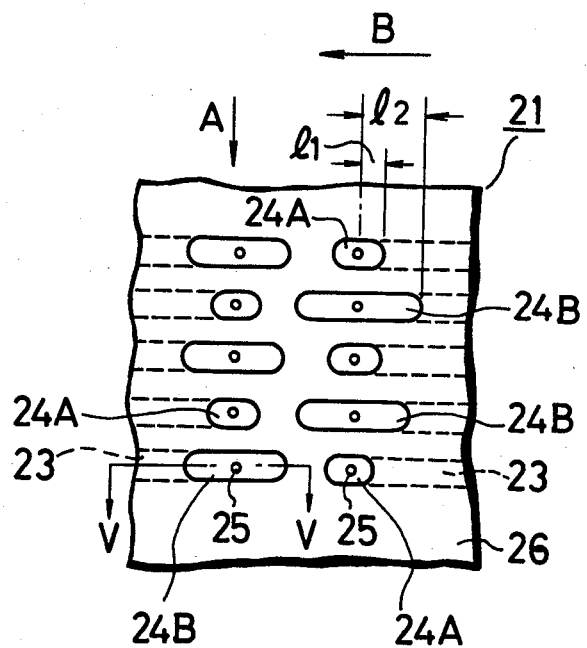
FIG. 1 is a top plan view showing a portion of a printed circuit board of a prior art.
Figure 2:
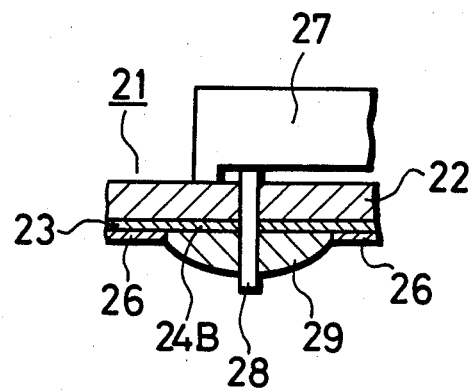
FIG. 2 is an enlarged cross-sectional view along a line V—V in FIG. 1.
Figure 3A:
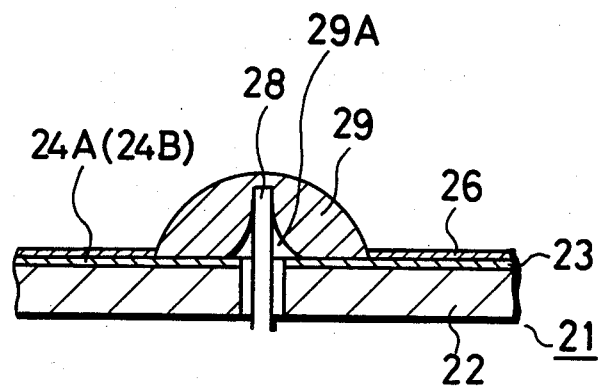
FIGS. 3A, 3B, and 3C are explanatory diagrams respectively showing different soldering conditions.
Figure 3B:
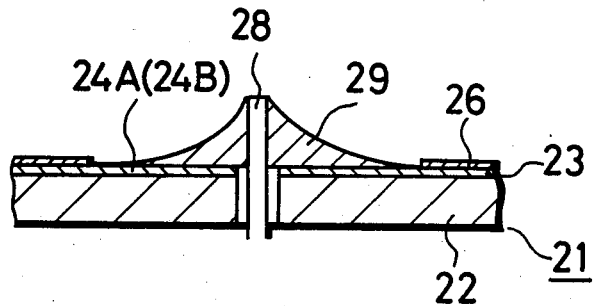
Figure 3C:
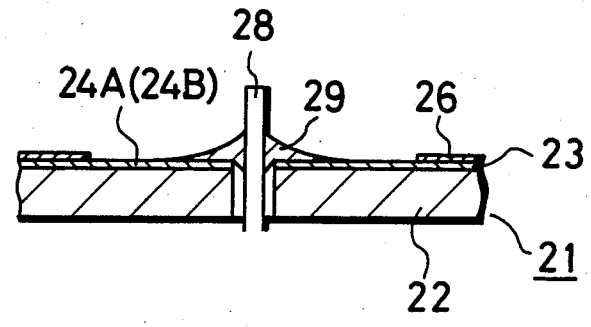
Figure 4:
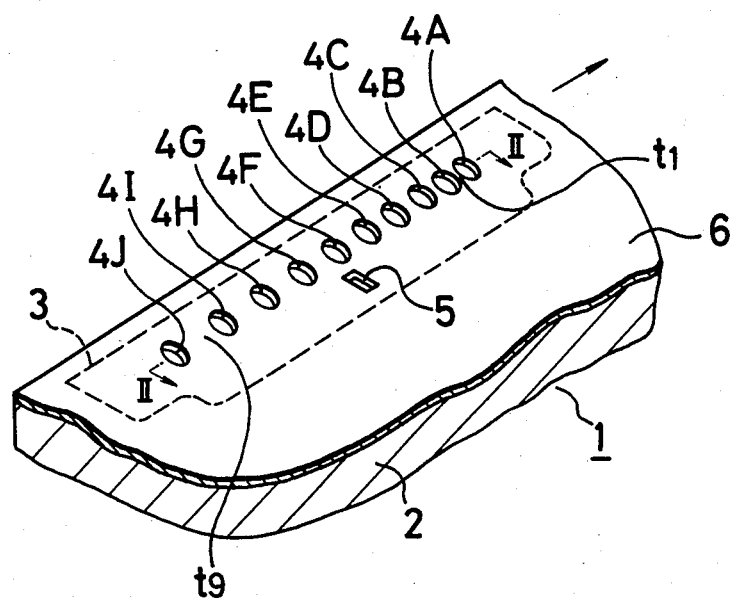
FIG. 4 is a perspective view showing a part of an embodiment of a printed circuit board according to the present invention.
Figure 5:
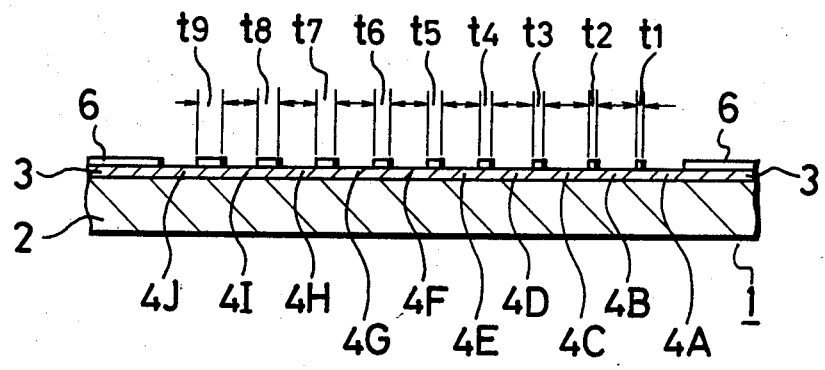
FIG. 5 is an enlarged cross-sectional view taken along a line II—II in FIG. 4.

FIG. 4 is a perspective view showing a part of an embodiment of a printed circuit board according to the present invention, and FIG. 5 an enlarged cross-sectional view taken along a II—II line in FIG. 4.

In FIGS. 4 and 5, reference numeral 1 designates a printed circuit board which includes an insulative subatrate 2, an electroconductive layer 3, and a resist layer 6. On the electrically insulative substrate 2, there is formed the electroconductive layer 3 which has formed thereon openings or land portions (hereinafter simply called "land portion") 4A–4J for soldering, all of which are formed in a same size and shape. The land portions 4A–4J are formed on the layer 3 by the resist layer 6 in such a manner that the intervals or distances between two adjacent land portions of a row of the land portions 4A–4J are increasing e.g. from 0.18 mm by a predetermined length, e.g. 0.04 mm. In this case, the shape of each of land portions is, for example, an oval. The distance between the centers of the land portions 4E and 4F positioned at middle portions of the row of the land portions 4A–4J is set at 1.78 mm which is suitable for mounting an IC, and the distance between the adjacent edges of the land portions 4E and 4F is selected at 0.34 mm. A mark 5 indicating a central interval or distance $t_5$ is also formed on the elecroconductive layer 3 by the resist layer 6. To be specific, the intervals between adjacent two land portions gradually increase by 0.04 mm, e.g. an interval $t_1$ between the land portions 4A and 4B is set at 0.18 mm, an interval $t_2$ between the land portions 4B and 4C at 0.22 mm, and an interval $t_9$ between the land portions 4I and 4J at 0.50 mm.

Figure 6A:
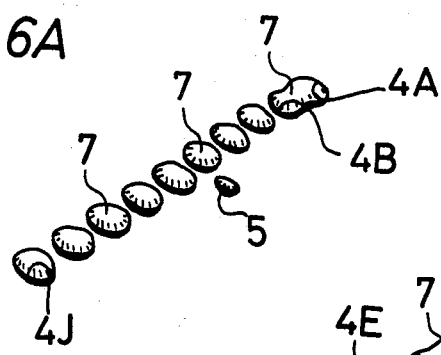
FIGS. 6A, 6B, and 6C are explanatory diagrams respectively showing examples of detection of the wettabilities of solder.
Figure 6B:
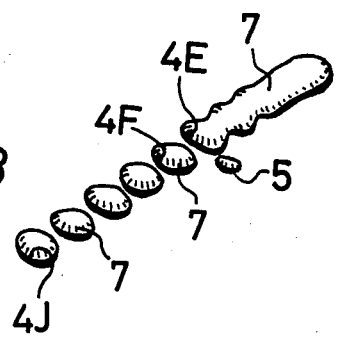
Figure 6C:
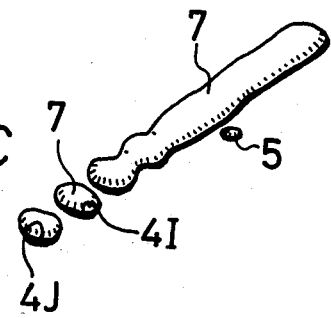

When the printed circuit board 1 according to the invention formed as described above is transported in the direction shown by an arrow in FIG. 4 in a solder bath (not shown) for soldering, solders 7 adhere to the row of the land portions 4A–4J, as shown in FIGS. 6A, 6B, and 6C, depending upon soldering conditions.

It can be seen from FIG. 6A that, as the solder bridging is produced only between the land portions 4A and 4B, the wettability of solder is excessively small. On such occasions, it is necessary to increase the wettability of solder by adjusting working speed, flux condition, pre-heat temperature, temperature of solder, flow rate of solder, etc., so as to obtain an adequate wettability of solder with which the soldering condition becomes as shown in FIG. 6B, which will be described later.

FIG. 6B shows that the solder bridging is produced between the adjacent land portions 4A to 4E, but not between the adjacent land portions 4F to 4J. This shows an adequate wettability of solder. It may be therefore anticipated that satisfactory soldering will be made for a printed circuit board for an IC having land portions whose center-to-center distance or pitch is 1.78 mm and whose width is 1.44 mm.

It can be seen from FIG. 6C that the solder bridging is produced between almost all of the adjacent land portions 4A to 4H, whereby it is judged that the wettability of solder is excessively large. Therefore, the wettability of solder should be decreased by adjusting the solder temperature or the like so as to obtain an adequate wettability of solder with which the soldering condition shown in FIG. 6B is obtained.

As described above, the printed circuit board according to the invention is provided with a checking pattern for detecting the soldering condition. It is therefore possible to evaluate the wettability of solder and ascertain the same by visually inspecting the condition of the solder bridging produced on the checking pattern while the electronic parts are being soldered on the printed circuit board. As a result, the wettability of solder can be adjusted on the basis of the evaluated data to an adequate value and hence the adequate soldering can be always carried out.

Further, as the wettability of solder can be detected as the evaluated value, it can be set uniformally at the optimum value, without the experiences, knowledge and so on of operators.

Furthermore, the checking pattern for detecting the soldering condition can be formed in a space such as an earth pattern or the like, it is possible to provide the checking pattern on the printed circuit board, without incurring an increase in cost.

In the above described embodiment, although the intervals $t_1$–$t_9$ between the two adjacent land portions of the land portions 4A–4J are increased in step by 0.04 mm, it is possible that the intervals are simply increased without a specific value. Also, it is possible to provide the land portions 4A–4J at the central location of the printed circuit board 1 so as to facilitate the detection of the wettability of solder.

As set forth above, the printed circuit board according to the invention is provided with a checking pattern having a row of land portions for detecting soldering condition, wherein the intervals between two adjacent land portions are sequentially increasing from one end to the other end of the row by a predetermined value. With this printed circuit board the wettability of solder can be set to an adequate value for a soldering by visually examining the solder bridging on the checking pattern. Therefore, the soldering can be satisfactorily made, without variations in the soldering conditions according to operators who are involved in the soldering procedure.

The above description is given on a single preferred embodiment of the invention but it will be apparent that many modifications and variations could be effected by one skilled in the art without departing from the spirits or scope of the novel concepts of the invention so that the scpoe of the invention should be determined by the appended claims only.

We claim as our Invention:

1. A printed circuit board comprising:
   an electrically insulative substrate;
   an electroconductive layer formed on said electrically insulative substrate; and
   a resist layer formed on said electroconductive layer and having a row of openings, distances between adjacent openings increasing from one end to another end of said row.

2. A printed circuit board according to claim 1, in which said distances increase by a predetermined value.

3. A printed circuit board according to claim 1, in which said openings are ovals of a same size and said distance is between two edges of adjacent ovals.

4. A printed circuit board according to claim 3 further comprising a center mark about the center of said row.

5. A printed circuit board according to claim 4, in which said center mark is an opening which is formed adjacent to said row in said resist layer.

6. A printed circuit board according to claim 5, in which said row is formed on the edge of said printed circuit board.

* * * * *